United States Patent [19]

Jang

[11] Patent Number: 5,462,530
[45] Date of Patent: Oct. 31, 1995

[54] INTRAVASCULAR CATHETER WITH BAILOUT FEATURE

[76] Inventor: G. David Jang, 636 Golden West Dr., Redlands, Calif. 92373

[21] Appl. No.: 157,663

[22] Filed: Nov. 23, 1993

Related U.S. Application Data

[63] Continuation-in-part of Ser. No. 865,975, Apr. 9, 1992, Pat. No. 5,263,932.

[51] Int. Cl.⁶ .................................................. A61M 29/00
[52] U.S. Cl. ............................................................. 604/160
[58] Field of Search ................................ 604/96, 101, 49, 604/53, 95, 102, 160; 606/191–194

[56] References Cited

U.S. PATENT DOCUMENTS

| | | |
|---|---|---|
| Re. 31,855 | 3/1985 | Osborne . |
| 3,297,030 | 1/1967 | Czorny et al. . |
| 3,550,591 | 12/1970 | MacGregor . |
| 3,682,173 | 8/1972 | Center . |
| 3,853,130 | 12/1974 | Sheridan . |
| 4,054,136 | 10/1977 | von Zeppelin . |
| 4,079,738 | 3/1978 | Dunn et al. . |
| 4,175,564 | 11/1979 | Kwak . |
| 4,411,055 | 10/1983 | Simpson et al. . |
| 4,411,654 | 10/1983 | Boarini et al. . |
| 4,569,347 | 2/1986 | Frisbie . |
| 4,573,470 | 3/1986 | Samson et al. . |
| 4,581,017 | 4/1986 | Sahota . |
| 4,585,013 | 4/1986 | Harris . |
| 4,619,644 | 10/1986 | Scott . |
| 4,631,056 | 12/1986 | Dye . |
| 4,631,059 | 12/1986 | Wolvek et al. . |
| 4,705,507 | 11/1987 | Boyles . |
| 4,738,666 | 4/1988 | Fuqua . |
| 4,747,833 | 5/1988 | Kousai et al. . |
| 4,748,982 | 6/1988 | Horzewski et al. . |
| 4,762,129 | 8/1988 | Bonzel . |
| 4,771,777 | 9/1988 | Horzewski et al. . |
| 4,813,930 | 3/1989 | Elliott . |
| 4,883,468 | 11/1989 | Kousai et al. . |
| 4,888,000 | 12/1989 | McQuilkin et al. . |
| 4,944,745 | 7/1990 | Sogard et al. . |
| 4,947,964 | 8/1990 | Shockey et al. . |
| 4,958,634 | 9/1990 | Jang . |
| 4,983,167 | 1/1991 | Sahota . |
| 4,988,356 | 1/1991 | Crittenden et al. . |
| 4,997,424 | 3/1991 | Little . |
| 5,040,548 | 8/1991 | Yock . |
| 5,046,503 | 9/1991 | Schneiderman . |
| 5,061,273 | 10/1991 | Yock . |
| 5,102,403 | 4/1992 | Alt . |
| 5,135,535 | 8/1992 | Kramer . |
| 5,154,725 | 10/1992 | Leopold . |
| 5,205,822 | 4/1993 | Johnson et al. . |
| 5,263,932 | 11/1993 | Jang .................................. 604/96 |
| 5,290,247 | 3/1994 | Crittenden . |

FOREIGN PATENT DOCUMENTS

| | | |
|---|---|---|
| 3934695 | 4/1991 | Germany . |
| 8203558 | 10/1982 | WIPO . |
| 9207606 | 5/1992 | WIPO . |

*Primary Examiner*—C. Fred Rosenbaum
*Assistant Examiner*—Manuel Mendez
*Attorney, Agent, or Firm*—Knobbe, Martens, Olson & Bear

[57] ABSTRACT

An intravascular catheter, comprising a catheter shaft having a proximal end, a distal portion, and a distal end, having diagnostic or therapeutic means mounted on the distal portion, and a bailout lumen extending along the catheter shaft from a point ordinarily outside the patient during use to a point proximal of the balloon and normally inside the patient during such use, the bailout lumen adapted to receive a removable guidewire and having an outer wall, with the outer wall preferably including a means such as a longitudinally extending slit for laterally removing the catheter from the patient and off of the guidewire while maintaining the position of the guidewire in the patient, and optionally including a side port through the outer wall of the bailout lumen through which a guidewire can be inserted. Methods for using the catheter are also disclosed.

15 Claims, 11 Drawing Sheets

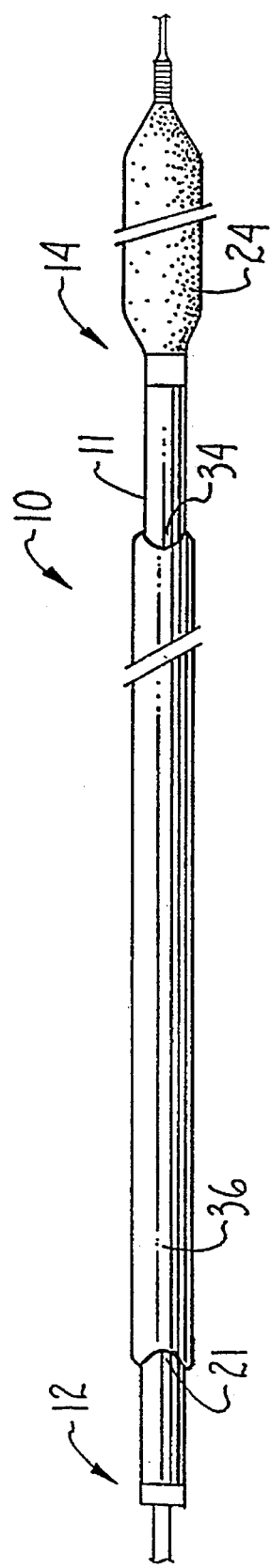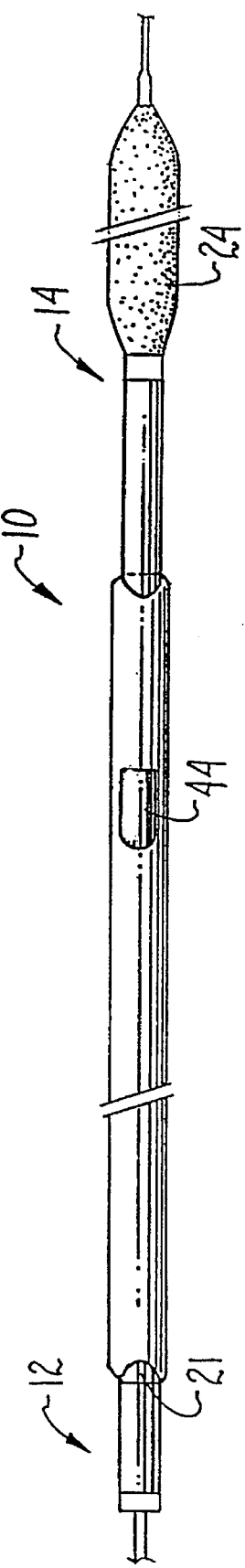

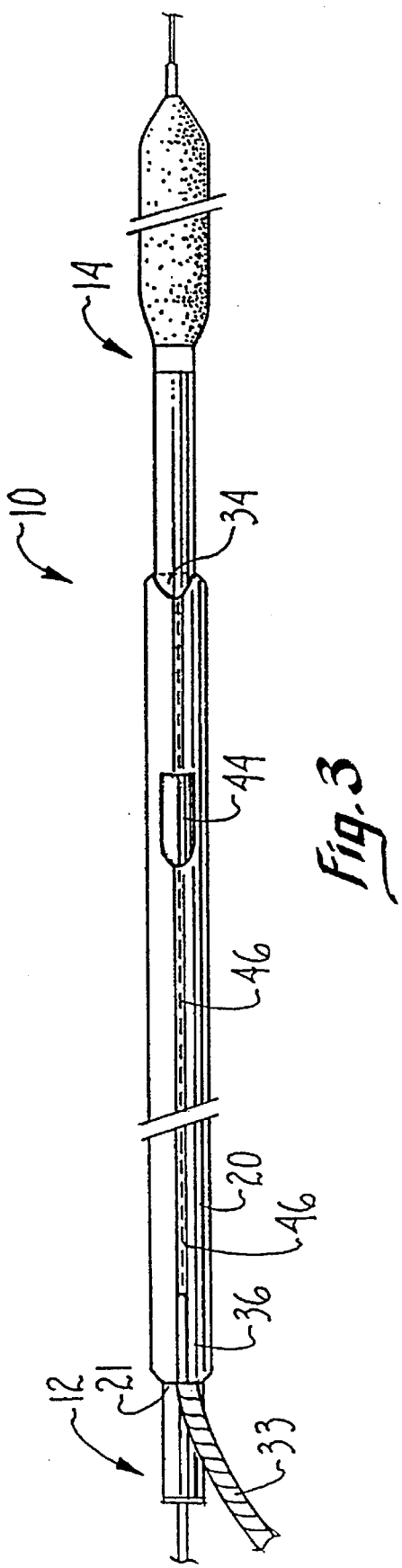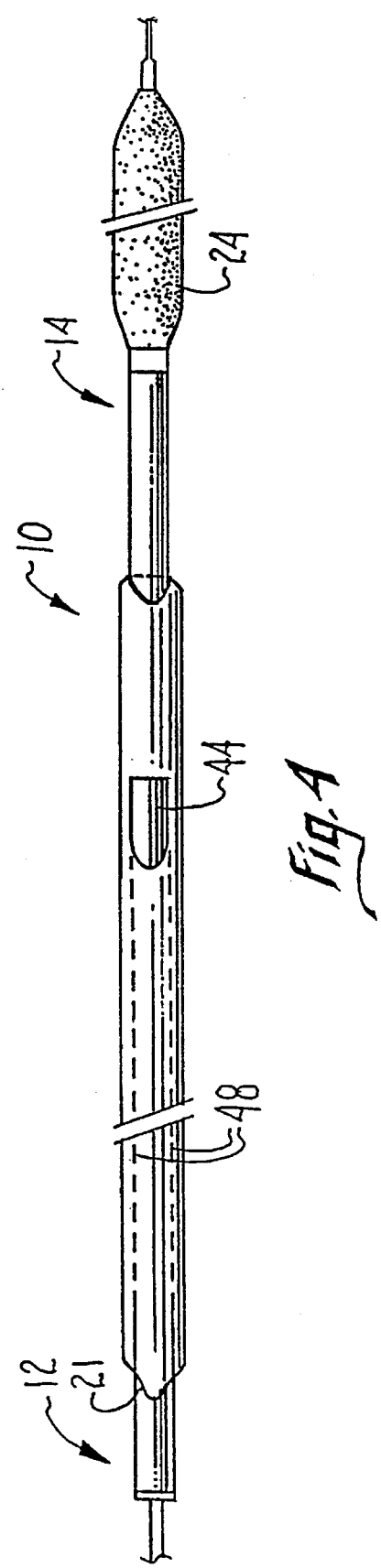

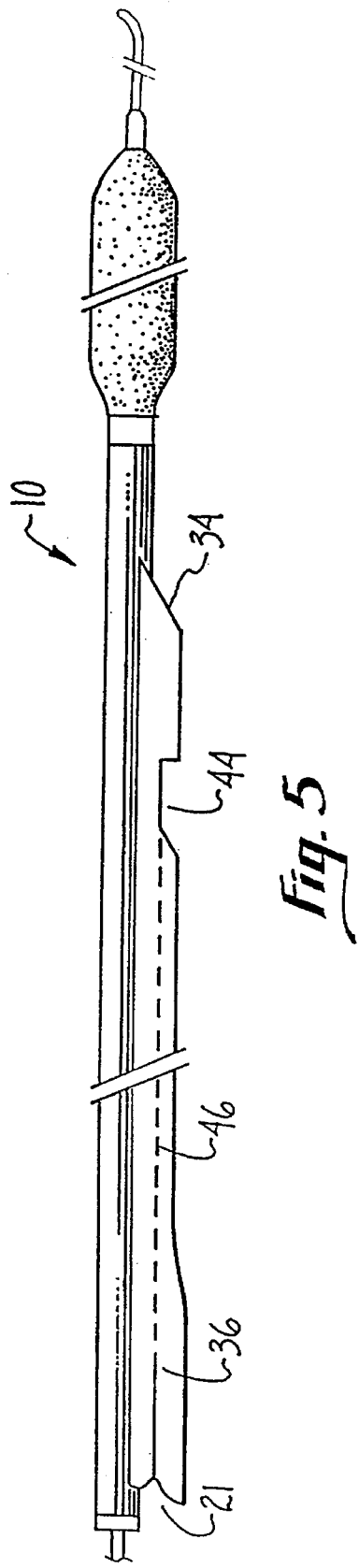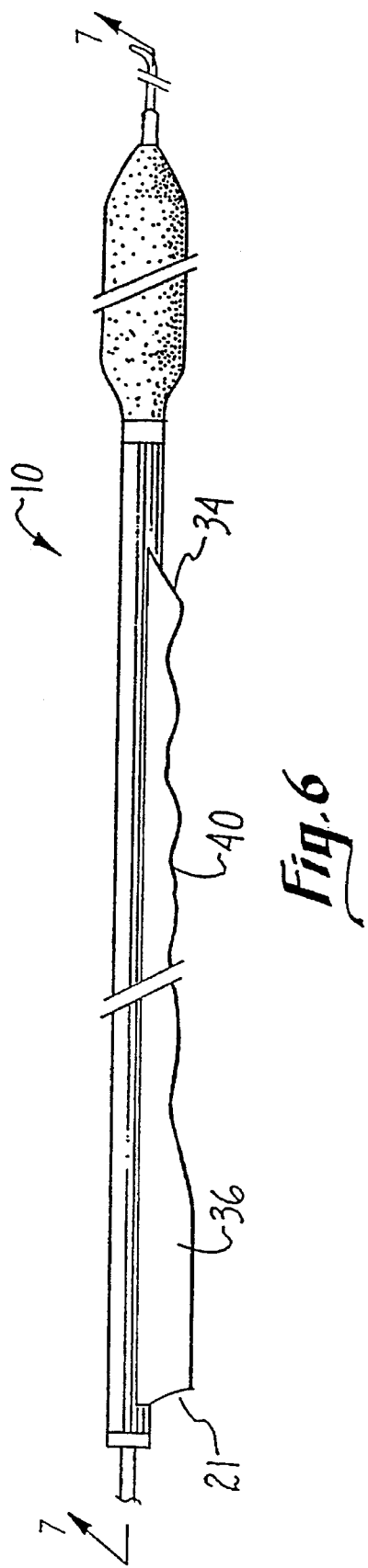

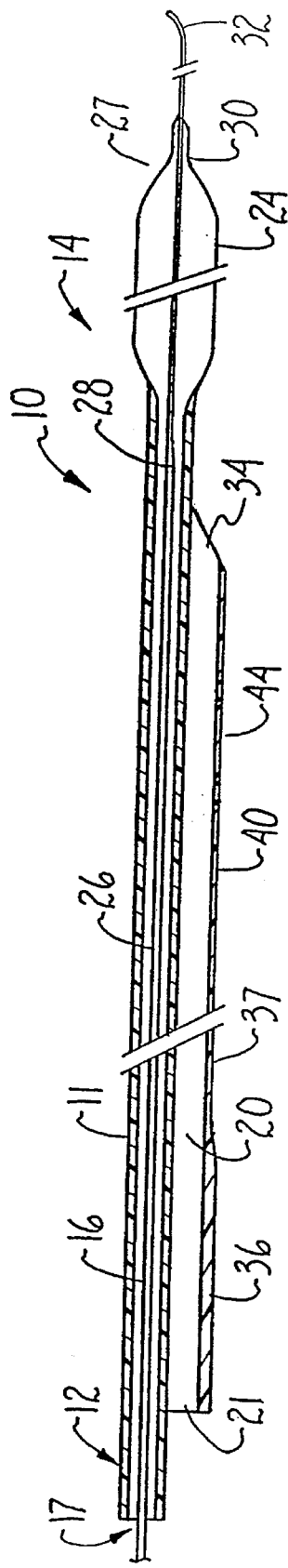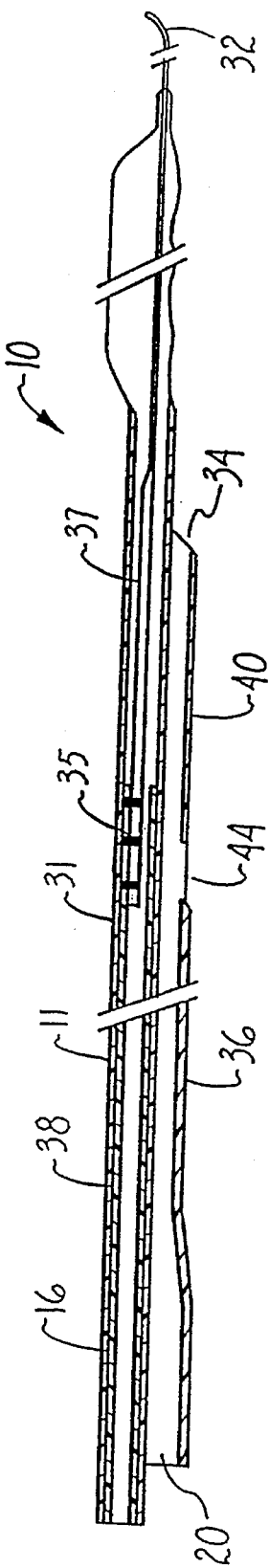

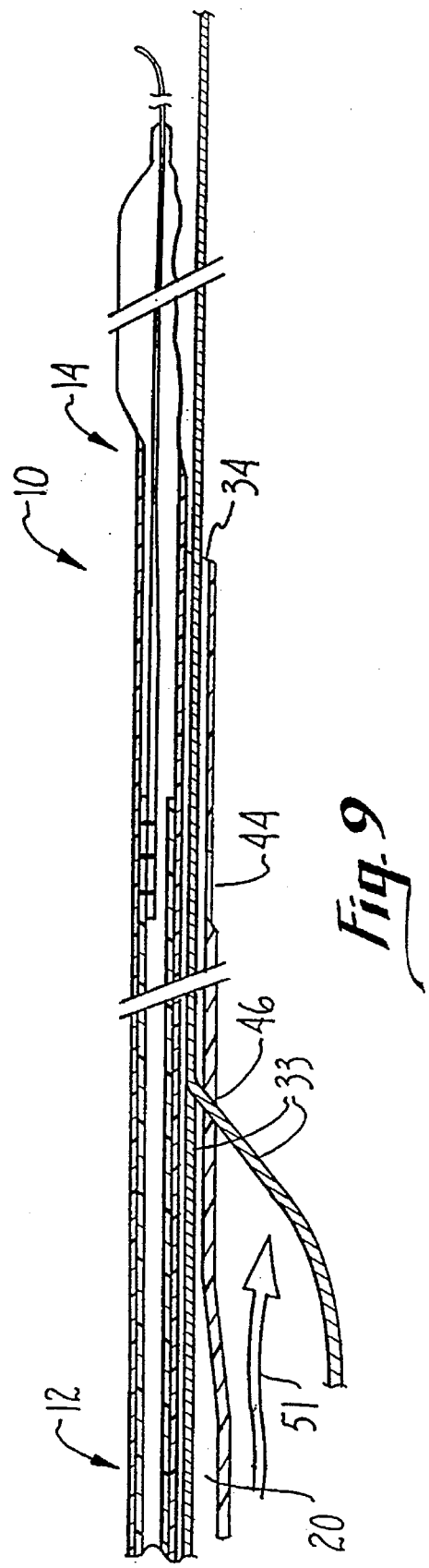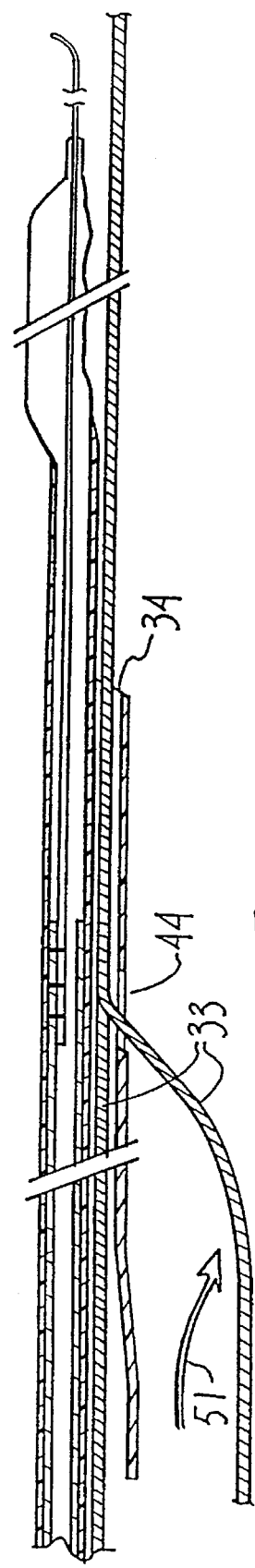

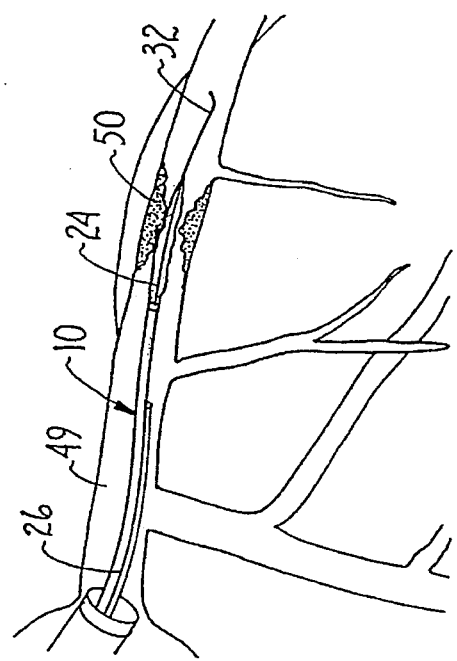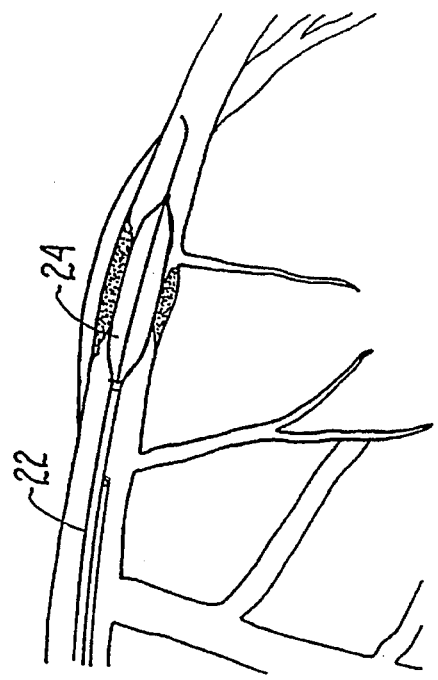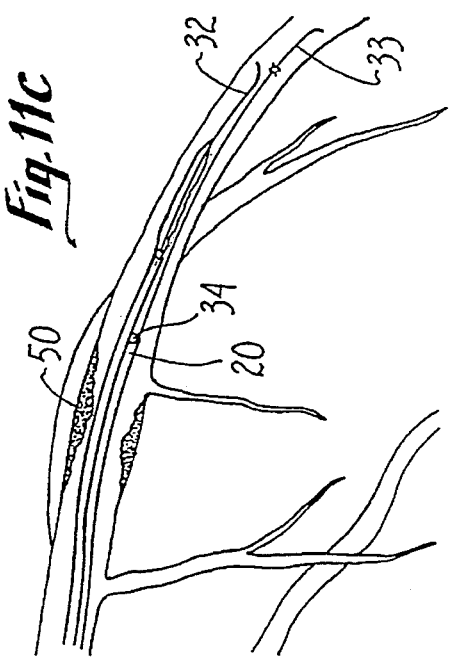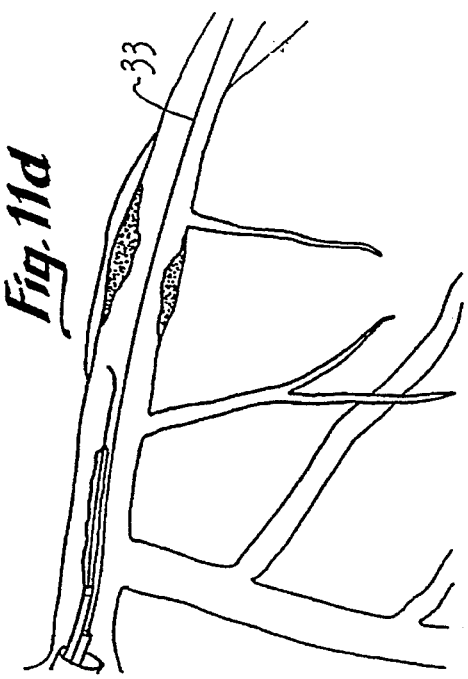

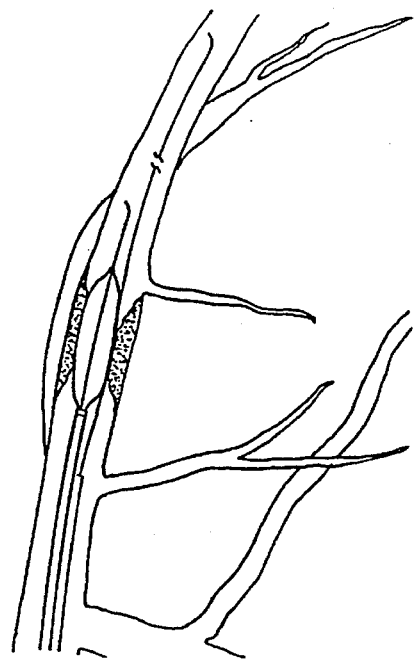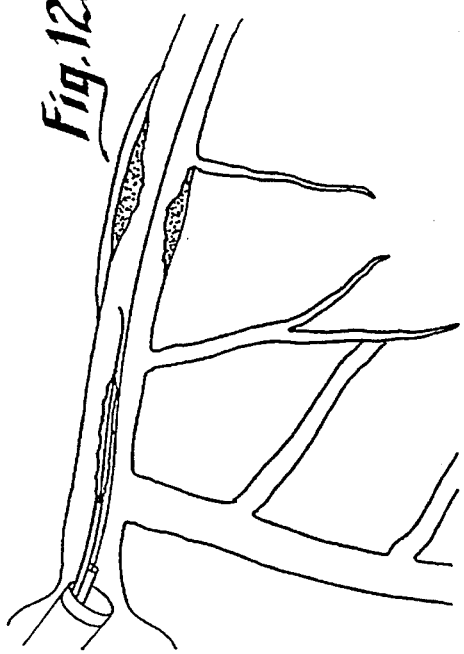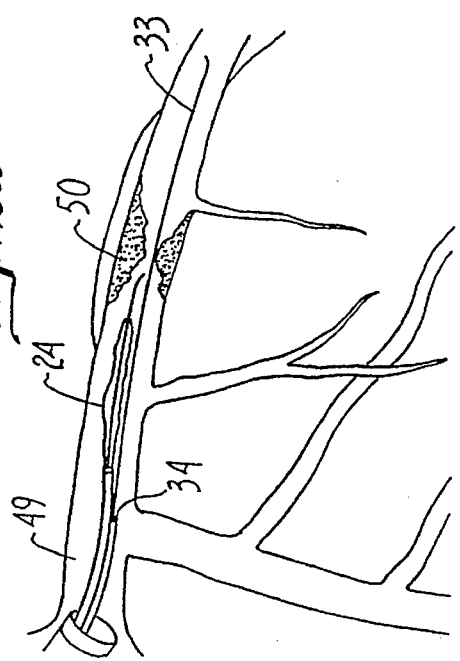

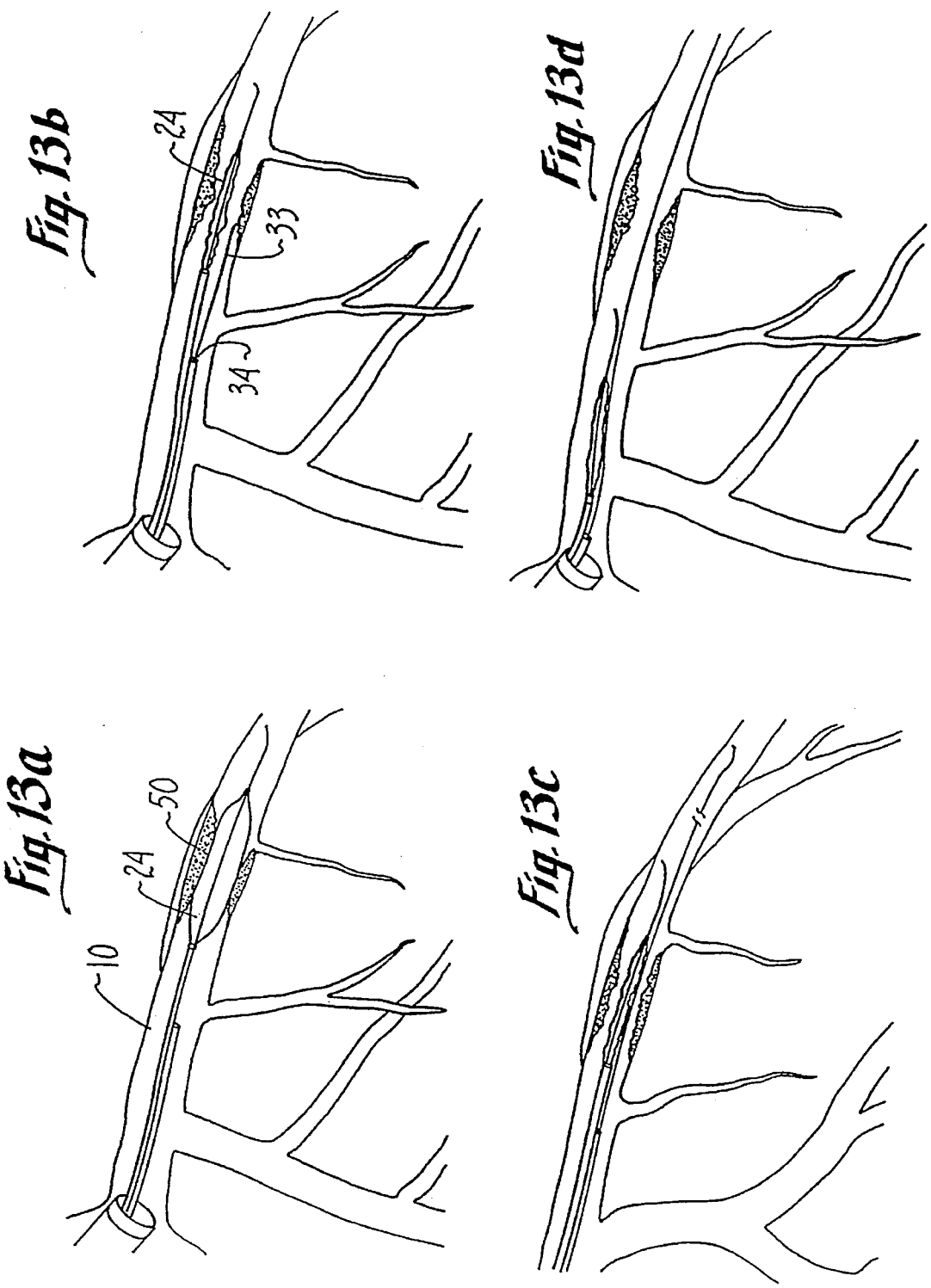

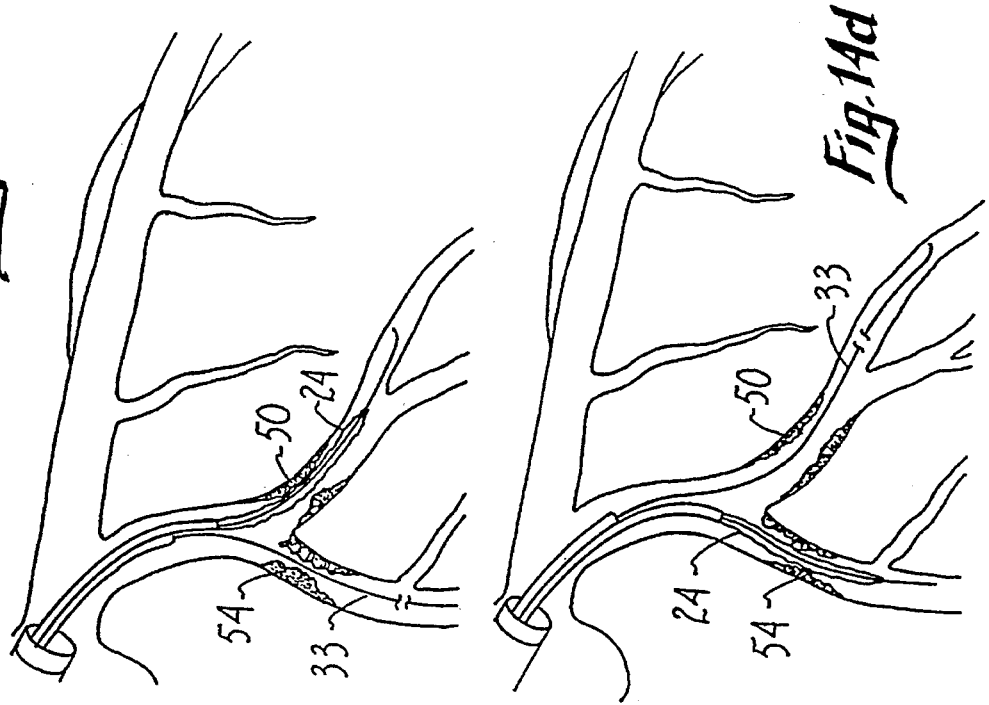

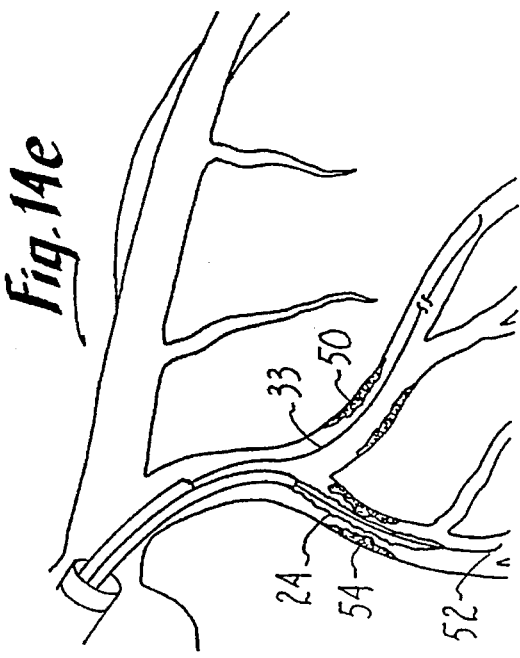
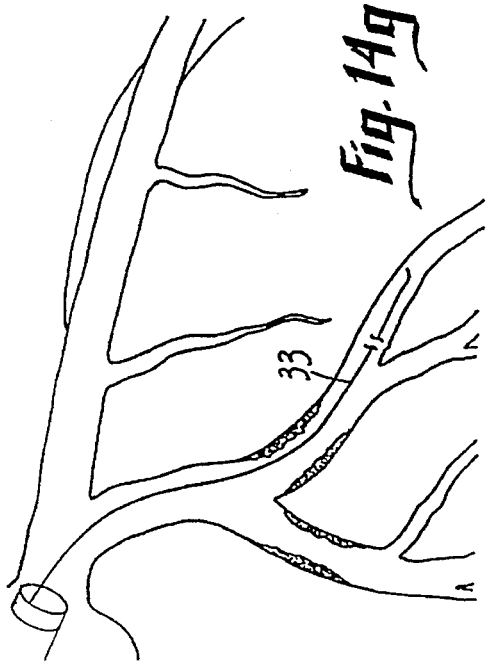

INTRAVASCULAR CATHETER WITH BAILOUT FEATURE

CROSS REFERENCE TO RELATED APPLICATIONS

The present application is a continuation in part application of U.S. patent application Ser. No. 07/865,975, filed Apr. 9, 1992, now U.S. Pat. No. 5,263,932.

BACKGROUND OF THE INVENTION

Percutaneous transluminal coronary angioplasty (PTCA) has emerged as the major viable present alternative to bypass surgery for revascularization of stenotic and occluded coronary arteries. Although transluminal angioplasty has application in peripheral artery disease, it is most widely used in the treatment of coronary artery disease. Unlike bypass surgery, percutaneous angioplasty does not require general anesthesia, cutting of the chest wall, extracorporeal perfusion, or transfusion of blood. Percutaneous coronary angioplasty is not only less invasive and less traumatic to the patient, it is also less expensive because the angioplasty patient will have a shorter hospital stay and shorter post-procedure recovery time.

Percutaneous transluminal angioplasty is performed by making a skin puncture with a specially-designed needle in one of the groins, and then introducing a guiding catheter into the aorta and coronary artery orifice. A smaller caliber catheter with a built-in inflatable and deflatable balloon of predetermined size and diameter is passed through the guiding catheter which is positioned in the orifice of a target artery. This balloon catheter (with the balloon totally deflated by negative pressure) is advanced inside the target coronary artery toward the point of obstruction in need for dilation.

The guidewire plays an essential role in leading the balloon catheter to the target coronary artery in safe and non-traumatic fashion. With the balloon portion of the catheter properly positioned inside the obstructed arterial segment, under X-ray fluoroscopic observation, the balloon is inflated by injecting contrast media mixed with saline at a pressure sufficient to overcome the resistance of the arteriosclerotic plaque of the obstructed segment.

By inflating the balloon in the stenosis multiple times over a period of between 10–30 seconds and one or two minutes (allowing blood flow between inflations), the desired dilation of the obstructed arterial segment can be achieved. After dilation, the guiding catheter, the balloon catheter (with the balloon completely deflated by negative pressure) and the guidewire are withdrawn from the artery and the patient, and the procedure is successfully terminated.

The size and diameter of the balloon to be used in transluminal angioplasty should be approximately matched to the size and native diameter of the obstructed arterial segment to be dilated. If the balloon size and diameter is smaller than the native artery, the results of balloon angioplasty are suboptimal, requiring a second dilation with a larger-sized balloon. If the balloon size is too large for the native artery, complications may occur due to arterial wall damage.

Conventional over-the-wire angioplasty catheters, with a guidewire lumen extending their entire length, permit simple guidewire exchange. However, conventional designs do not permit efficient catheter exchange without the use of an extension wire. Another type of angioplasty catheter has a guidewire permanently attached to the catheter at the distal end. This fixed wire, low profile catheter can be manufactured with a small overall diameter since there is no separate guidewire lumen. The guidewire in this type of catheter is referred to herein as a torquewire. Fixed wire catheters, although being preferred by many physicians because of their small diameter, have no provision for rapid replacement of either the torquewire or catheter. If, for example, balloon replacement becomes necessary once the catheter is positioned at a stenosis, the entire catheter must be removed and the balloon catheter reinserted into the artery, starting the procedure over again. Similarly, if the torquewire tip must be reshaped or replaced, the only option is removal of the entire catheter. Currently available fixed wire catheters do not have the benefit of rapid replacement.

Emergency situations can also arise during or after angioplasty. For instance, after balloon dilation, the vessel wall may collapse, requiring immediate insertion of a perfusion catheter. Accordingly, there is a need for a system for the rapid-exchange of vascular catheters, whether the catheter is a fixed wire catheter or other design, such as an over-the-wire catheter.

SUMMARY OF THE INVENTION

In accordance with a first aspect of the present invention, there is provided an intravascular catheter, comprising a catheter shaft having a proximal end, a distal portion, and a distal end, and having diagnostic or therapeutic means mounted on the distal portion, a bailout lumen having a proximal opening and a distal opening, the lumen extending along the catheter shaft from a point within about 30 cm of the proximal end of the catheter to a point proximal to and within about 30 cm of the diagnostic or therapeutic means, the bailout lumen adapted to receive a removable guidewire and having an outer wall, the outer wall further comprising a side port extending therethrough, located between the proximal opening and the distal opening, the side port adapted to permit a guidewire to extend therethrough to pass through a distal portion of the bailout lumen. In a preferred embodiment, the catheter further comprises guidewire removing means, adapted for removing a guidewire laterally out of the bailout lumen.

In accordance with a second aspect of the present invention, there is provided an intravascular catheter, comprising a catheter shaft having a proximal end, a distal portion, and a distal end, and having diagnostic or therapeutic means mounted on the distal portion, a bailout lumen having a proximal opening and a distal opening, the lumen extending along the catheter shaft from a point within about 30 cm of the proximal end of the catheter to a point proximal to and within about 30 cm of the diagnostic or therapeutic means, the bailout lumen adapted to receive a removable guidewire and having an outer wall, the outer wall further comprising guidewire removing means extending from the proximal opening of the bailout lumen distally toward the diagnostic or therapeutic means at least 30 cm., the guidewire removing means being adapted to permit a guidewire extending through the bailout lumen to be removed laterally through the outer wall. In a preferred embodiment, the outer wall has a side port extending therethrough, the side port located between the proximal and distal ends of the bailout lumen and adapted to permit a guidewire to extend therethrough to pass through a distal portion of the bailout lumen.

In accordance with a third aspect of the present invention, there is provided an angioplasty catheter, comprising a catheter shaft having a proximal end, a distal portion, and a distal end, with a balloon inflation lumen extending therethrough, an angioplasty balloon on the distal portion of the catheter operatively communicating with the balloon inflation lumen for inflation and deflation of the balloon, and a bailout lumen having a proximal opening and a distal opening, the lumen extending along the catheter shaft from a point within about 30 cm of the proximal end of the catheter to a point proximal to and within about 30 cm of the balloon, the bailout lumen adapted to receive a removable guidewire and having an outer wall, the outer wall further comprising a side port extending therethrough, located between the proximal opening and the distal opening, the side port adapted to permit a guidewire to extend therethrough to pass through a distal portion of the bailout lumen. In a preferred embodiment, the catheter further comprises guidewire removing means, adapted for removing a guidewire laterally out of the bailout lumen.

In accordance with a fourth aspect of the present invention, there is provided an angioplasty catheter, comprising a catheter shaft having a proximal end, a distal portion, and a distal end, with a balloon inflation lumen extending therethrough, an angioplasty balloon on the distal portion of the catheter operatively communicating with the balloon inflation lumen for inflation and deflation of the balloon, and a bailout lumen having a proximal opening and a distal opening, the lumen extending along the catheter shaft from a point within about 30 cm of the proximal end of the catheter to a point proximal to and within about 30 cm of the balloon, the bailout lumen adapted to receive a removable guidewire and having an outer wall, the outer wall further comprising guidewire removing means extending from the proximal opening of the bailout lumen distally toward the balloon at least 30 cm., the guidewire removing means being adapted to permit a guidewire extending through the bailout lumen to be removed laterally through the outer wall. In a preferred embodiment, the outer wall has a side port extending therethrough, the side port located between the proximal and distal ends of the bailout lumen and adapted to permit a guidewire to extend therethrough to pass through a distal portion of the bailout lumen.

BRIEF DESCRIPTION OF THE DRAWINGS

FIG. 1 is an on-face ventral view of one embodiment of the present bailout catheter.

FIG. 2 is an on-face ventral view of one embodiment of the present bailout catheter incorporating a distal side port.

FIG. 3 is an on-face ventral view of one embodiment of the present bailout catheter incorporating a distal side port and a longitudinal guidewire removing means.

FIG. 4 is an on-face ventral view of one embodiment of the present bailout catheter incorporating a distal side port and longitudinal guidewire removing means formed by parallel slits.

FIG. 5 is an external profile view of the catheter of FIG. 4.

FIG. 6 is an external profile view of one embodiment of the present bailout catheter incorporating a collapsible guidewire lumen.

FIG. 7 is a longitudinal cross-section of the fixed wire balloon catheter of FIG. 6, taken along the line 7—7.

FIG. 8 is a longitudinal cross-section of a fixed wire balloon catheter incorporating a hypotube and a distal side port.

FIG. 9 is a longitudinal cross section of the fixed wire balloon catheter of FIG. 8, showing lateral movement of a guidewire out of a bailout lumen for rapid exchange function.

FIG. 10 is a longitudinal cross section of the fixed wire balloon catheter of FIG. 9 showing a completed lateral guidewire transfer.

FIG. 11a–11d, illustrate a clinical angioplasty procedure using the fixed-wire bailout features.

FIG. 12a–12d, illustrate an alternative clinical angioplasty procedure using the inventive bailout catheter.

FIG. 13a–13d, illustrate another clinical angioplasty procedure using the inventive bailout catheter.

FIG. 14a–14d, illustrate a clinical angioplasty procedure at a vessel bifurcation on dual stenoses using the inventive features of the catheter.

DETAILED DESCRIPTION

Figure 15:
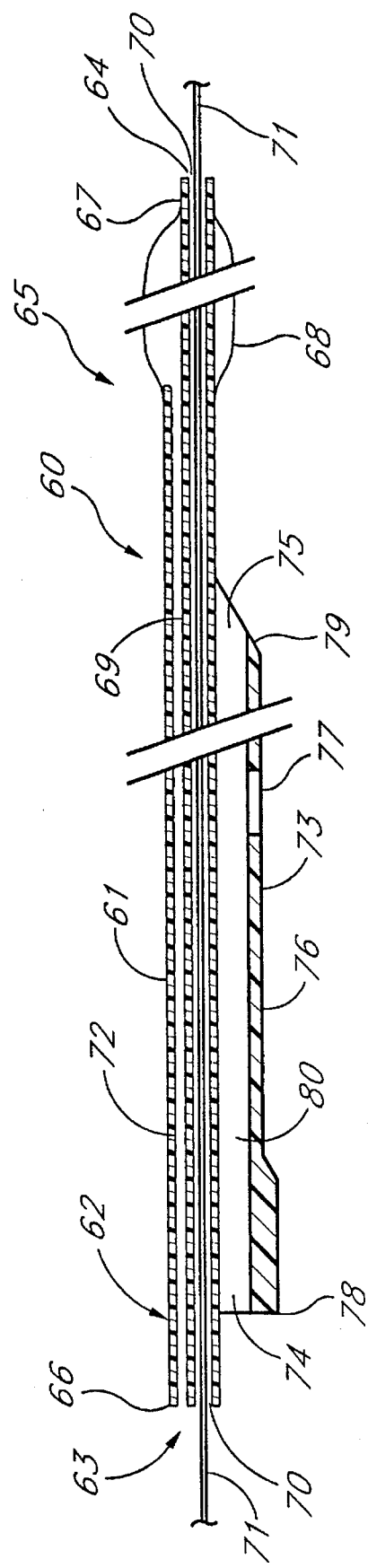
FIG. 15 illustrates a longitudinal cross-sectional view of an over-the-wire angioplasty catheter incorporating the bailout lumen in accordance with the present invention.

In accordance with one aspect of the present invention, there is provided an angioplasty catheter that combines the advantages of a low profile, fixed wire catheter with the benefits of rapid guidewire and catheter exchange. In accordance with another aspect of the present invention, there is provided a vascular catheter having the benefits of rapid-exchange.

Bailout of Fixed Wire Catheters

In accordance with the first aspect of the invention, the present invention provides a low profile, fixed wire catheter containing an exterior, preferably collapsible, bailout lumen. The bailout lumen is a longitudinal receptacle or channel running distally from the proximal end of the catheter shaft to a point just proximal of the angioplasty balloon. A guidewire can be inserted into this bailout lumen in the event a catheter exchange becomes necessary during an angioplasty procedure.

During such an exchange, a guidewire is inserted into the proximal end of the bailout lumen so that it fully traverses the lumen and protrudes a distance from the distal end. The fixed wire catheter can thereafter be removed proximally over the guidewire while keeping the guidewire tip immobile at, or distal to, the site of stenosis. A new catheter can then be rapidly and safely inserted to the same stenotic region by advancement over the inserted guidewire. The new catheter could be a perfusion catheter, a conventional over the wire catheter, a rapid exchange catheter, another fixed wire catheter having a bailout lumen, or any other device capable of being inserted over a guidewire. The combination of a low profile design and bailout lumen provides a vast improvement over currently available fixed wire angioplasty catheters.

Specifically, referring to FIG. 1, the fixed wire bailout catheter 10 of the present invention comprises a longitudinally extending catheter shaft 11 with a proximal end 12 and distal end 14. The catheter shaft 11 is preferably made of any suitable conventional polymer material, such as polyethylene, polyvinylchloride, polyethylene terephathalate, or other suitable materials. The catheter 10 preferably has an outer diameter of between F 3.0 and F 3.5 with the most preferable diameter being under F 3.5.

Overlaying one portion of the catheter shaft 11 is a bailout lumen wall 36 which forms the exterior portion of a bailout lumen 20 (not shown). The proximal end of the bailout lumen wall 36 defines an entry point 21 to the lumen 20. The distal edge of the bailout wall 36 defines the distal exit point 34 of the bailout lumen 20. Attached to the distal end of the catheter shaft 11 is an angioplasty balloon 24.

The balloon 24 is usually a generally cylindrical angioplasty balloon, and can be made in accordance with conventional techniques for fabricating angioplasty balloons. Preferably, it is either blown from the distal end 14 of the catheter shaft 11, or is blown or formed of a separate piece of material which is bonded to the distal end 14 of the catheter shaft 11. The balloon 24 may advantageously be formed of relatively inelastic polymer material, such as polyethylene, polypropylene, polyvinylchloride, polyethylene terephthalate, or similar materials.

Referring now to FIG. 2, one preferred embodiment of the catheter 10 contains a distal side port 44 formed from the bailout lumen wall 36. The side port 44 is located distally of the proximal opening 21 of the bailout lumen, at a point normally inside of the patient when the catheter is properly in place for performance of an angioplasty procedure. Preferably, the side port 44 is located proximally of the balloon 24 and within 80 cm, preferably 60 cm, and more preferably within about 40 cm of the balloon 24. It is further contemplated that the side port can be used as a perfusion port, permitting the catheter 10 to be used as a perfusion catheter. In this embodiment, the side port 44 is preferably located relatively close to the balloon, perhaps within about 5 cm, and the bailout lumen extends to within about 1 or 2 cm of the balloon. The side port 44 need not be adapted to receive a guidewire when its function is solely as a perfusion port, and could in that event comprise multiple smaller openings into the bailout lumen. In using the catheter 10 as a perfusion catheter, the catheter is advanced so that the side port 44 is on one side of a lesion and the distal point 34 is located on the other side of the lesion. This permits blood to enter the side port 44 and exit the distal point 34, thereby traversing the lesion. The bailout lumen is preferably non-collapsible when used as a perfusion catheter.

The catheter 10 of the present invention can advantageously be provided with a removal means 46 for removing a guidewire 33 out of the bailout lumen 20 through the outside wall 36 as shown in FIG. 3. If the catheter shaft 11 or the guidewire 33 is considered to extend in a longitudinal or axial direction, this guidewire movement out of the bailout lumen 20 can be considered as a lateral, sideways, radial, or transverse motion. The guidewire removing means 46 is adapted to provide a slit or other longitudinal opening through the outside wall 36 of the bailout lumen 20 through which the guidewire may be removed laterally from inside the bailout lumen 20. The guidewire removing means 46 may be an actual slit cut entirely through the side wall 36 of the bailout lumen 20. Alternatively, it may be an inchoate slit or perforated or weakened line. The guidewire removing means 46 may be cut entirely through the outside wall 36 of the bailout lumen 20, or only in certain sections, leaving other sections at least partially intact, to form a type of perforated line. The removal means 46 may be formed of the same material or a different material than the remainder of the catheter shaft 11 and even of a different material than the adjacent portions of the outside wall 36 of the bailout lumen 20. Combinations of fully formed slits and weakened areas or inchoate slits are also contemplated, such as having an inchoate slit in portions of the catheter normally outside the patient during use (eliminating backbleeding through the slit) and a fully formed slit in a portion of the catheter normally inside the patient during use. Although not the most preferred embodiment, one embodiment of FIG. 3 would contain the guidewire removal means 46 but without a distal side port 44. In one embodiment, the removal means extends substantially the entire distance from the guidewire lumen entrance 21 to the distal point 34.

One advantage of having only an inchoate slit is that it prevents backbleeding out of the guidewire removing means 46 during performance of the angioplasty procedure. It is possible, however, to have the guidewire removing means be formed from an inchoate slit in only the portion of the guidewire exposed to the patient's vasculature. The remainder of the guidewire removing means 46 that is inside the patient and inside the guiding catheter can be a fully formed slit or a perforated slit without creating backbleeding problems.

The guidewire removing means 46 is also contemplated to include other conformations, such as a removable tear strip 47 defined by a pair of parallel weakened lines 48 extending distally from the proximal opening 21, as shown in FIG. 4. In a preferred embodiment, the lines 48 at the very proximal end of the tear strip 47 are severed to form a tab. Pulling on the tab then removes the remainder of the tear strip 47 by severing the weakened areas 48.

FIG. 5 reveals a profile view of the embodiment of FIG. 4 wherein the guidewire removing means 46 comprises a tear away strip extending distally from the proximal opening 21 to the side port 44.

The guidewire removing means 46 normally extends from the proximal opening 21 (normally outside the patient) distally along the length of the bailout lumen 20 to a point that is ordinarily inside the patient when the catheter 10 is properly placed for performance of an angioplasty procedure (FIGS. 3, 4, 5). Thus, the guidewire removing means begins at a point ordinarily outside the patient and outside the guiding catheter upon proper placement of the catheter 10 and extends distally to a point ordinarily inside the patient upon such placement. Advantageously, the guidewire removing means 46 extends at least 50% of the length of the catheter shaft 11. From another perspective, the guidewire removing means 46 extends distally for at least 40 cm, preferably at least 60 or 70 cm, and more preferably at least 80, 90 or 100 cm. In one embodiment, the guidewire removing means can extend the entire length of the bailout lumen 20.

The guidewire removing means 46 may advantageously extend distally to the side port 44, and in one embodiment of the invention, may extend an additional distance distally beyond the side port 44. The guidewire removing means 46 preferably terminates proximally of the balloon 24, and may be immediately adjacent the balloon 24, at the distal end of the bailout lumen 20, or may be 2 cm, 5 cm, 10 cm, 20 cm, 30 cm, or more proximally of the balloon 24.

If the guidewire removing means 46 is not a slit prior to its use, it can become a slit or opening during its use. At the distal end of the removing means 46, the distal side port 44 can be used as the alternate entry point for the guidewire into the bailout lumen 20, especially for rapid back-loading in a catheter exchange.

The ability to remove the guidewire from almost the entire length of the bailout lumen 20 is important in catheter removal. In embodiments of the invention lacking a guidewire removing means 46, a guidewire extension must be attached to the proximal portion of the guidewire 33 to allow complete catheter removal from the patient. However, by laterally removing the guidewire 33 through the removal means 46, the catheter 10 can be retracted from the patient without an exterior guidewire extension.

The particular method of using the guidewire removing means is as follows. When the guidewire is to be removed radially or laterally out of the bailout lumen 20, the guidewire removing means 46 provides a slit or opening in the outside wall 36 of the bailout lumen 20 through which the guidewire 33 may be removed from the bailout lumen 20. This slit or opening, if not fully formed, may be completed by cutting the outside wall 36 of the bailout lumen 20, by tearing or rupturing a weakened area in the outside wall 36, or by tearing loose a removable strip. In a preferred embodiment the guidewire removing means 46 is a weakened area that is fully opened only after the guidewire 33 is removed through the guidewire removing means 46.

In one embodiment, the guidewire 33 simply tears open a slit through the outside wall 36 of the bailout lumen 20. Alternatively the outside wall 36 may be provided with a filament in association with the guidewire removing means 46. The filament may be a continuous fiber or strand extending along the length of the guidewire removing means and inside at least a portion of the outside wall 36 of the guidewire lumen 20. When the filament is pulled outwardly, it tears a slit into the outside wall 36 of the bailout lumen 20. It preferably begins either at the proximal end of the catheter 10 or within 5, 10, or 15 cm of the proximal end.

Preferably, once the slit is formed the guidewire is removed by securely holding the guidewire in position while pulling the catheter out of the patient. This results in the catheter being pulled off of the stationary guidewire as the catheter is removed from the patient.

The catheter of the present invention may be used as a rapid exchange catheter with the guidewire 33 extending through the side port 44 and out of the distal end 34 of the bailout lumen 20. Alternatively, it may be used as a conventional over the wire catheter with the guidewire 33 extending substantially the entire length of the catheter shaft 11 from the proximal end 21 longitudinally through the entire length of the bailout lumen 20 and out of the distal end 34 thereof.

In order for the distal end of the catheter 10 to be the smallest possible diameter, the outer shell of the bailout lumen 20 is optionally separated into the proximal thicker-walled portion 36 and a thinner-walled, collapsible, more distal portion 40 (FIG. 6). The thin-walled distal portion 40 can begin immediately distal (e.g., within 2 to 20 cm) of the proximal opening 21 of the guidewire lumen and continue longitudinally to the guidewire distal opening 34. Alternatively, the thin walled distal portion 40 can continue to a point well inside the patient during use of the catheter 10, or to a point just inside the guiding catheter. During advancement of the catheter 10 through the patient's vasculature, the thin-walled portion 40 of the bailout lumen 20 can collapse, thereby decreasing the overall circumference of the catheter's most distal portion. The more proximal portion of the guidewire wall 36 is preferably thicker, thereby allowing a guidewire removing means (not shown) to be maintained by polymer memory. A thicker guidewire wall 36 also facilitates the pushability characteristics of the catheter shaft.

As shown in FIG. 7, the thin-walled portion 40 of the bailout lumen 20 can extend from a point proximal to the side port 44 to a point distal to, and including the side port 44. Other embodiments of the thin wall 40, as illustrated in FIG. 8, include the thin wall being located only distal to side port 44 and continuing to the distal end of the bailout lumen 20.

FIG. 7 is a longitudinal cross-section cut along the line 6—6 of FIG. 6. The catheter 10 includes a balloon inflation lumen 16 extending distally through the catheter shaft 11, terminating distally at the distal end 14 of the catheter shaft 11 and in fluid connection with the balloon 24. Furthermore, FIG. 7 also illustrates the bailout lumen 20 running distally, at or about the proximal end 12 of the catheter shaft 11, along the catheter shaft 11, to a point somewhat proximal of the distal end 14 of the catheter shaft 11.

Fluid introduced into the proximal end 17 of the balloon inflation lumen 16 can travel distally through the catheter shaft 11 to inflate the angioplasty balloon 24. The bailout lumen 20 terminates approximately 1 cm to 10 cm, more preferably from 2 cm to 6 cm of the proximal end of balloon 24.

Longitudinally traversing the interior portion of the balloon inflation lumen 16 and balloon lumen 22 is a steerable torquewire 26 (FIG. 7). The torquewire 26 is preferably of a small enough diameter such that fluid introduced at the proximal opening 17 of the balloon inflation lumen 16 can pass around the torquewire 26 distally and flow into the balloon 24 without impediment. The torquewire 26 is preferably made of flexible metal material, such as stainless steel.

The torquewire 26 is permanently affixed to the distal end 27 of the balloon 24 at a connection point 30. In one preferable embodiment of the current invention, the torquewire 26 may be reduced in diameter at a torquewire reduction point 28. This reduction point 28 is normally located at the point where the balloon 24 and balloon inflation lumen 16 intersect. At the torquewire diameter reduction point 28, the torquewire 26 diameter can be reduced by up to 50 percent. Other embodiments having greater or lesser reductions or no reduction in torquewire diameter are also contemplated within the present invention.

The torquewire 26, which is directly connected to a distal floppy tip 32 is used by the operator to steer the catheter 10 through the patient's vasculature.

Attachment of the torquewire 26 to the balloon 24 at the distal connecting point 30 provides a means of steering the catheter 10 and the leading catheter tip 32. For example, clockwise rotation of the torquewire 26 correspondingly leads to a clockwise rotation of the catheter 10 and the tip 32. The torquewire 26 thereby provides a steerage means of the catheter 10 through the patient's vasculature.

The torquewire tip 32 defines the distal-most end of the catheter device 10 protruding a distance of between 1.0 cm and 3.0 cm from the connecting point 30. The torquewire tip 32 may be of conventional guidewire design, and is preferably shapeable by the physician.

Other variations of the fixed wire bailout catheter are also contemplated, such as the alternative design detailed in FIG. 8. In this embodiment of the present invention, a non-bioactive metal such as a stainless steel hypotube 31 forms at least a portion of the catheter shaft proximally of the balloon, and defines the balloon inflation lumen 16. The hypotube 31 preferably extends from the proximal end of the catheter 10 distally to a point preferably about 10 cm to 30 cm proximal to the balloon 24. The distal end of the hypotube 31 may be affixed to a shortened torquewire 37 at a point 35 in the interior of the catheter shaft 11. An operator's rotational movement of the hypotube 31 thereby causes rotation of both the catheter shaft 11 and truncated torquewire 37 providing a steerage means for the catheter 10. The hypotube 31 may advantageously be coated with a polymer material 38 to facilitate bonding between the bailout lumen and the catheter shaft.

The hypotube 31 imparts stiffness to the catheter 10, providing enhanced pushability and decreasing the tendency of the catheter shaft 11 to buckle.

Once the angioplasty procedure has been performed, by inflating the balloon 24 through fluid injection into the balloon inflation lumen 16, it sometimes becomes necessary to exchange the catheter 10 for an alternate catheter. This exchange may be necessary because the original balloon was an incorrect size for suitable performance of the angioplasty procedure, or an emergency situation, such as vascular collapse, may require the insertion of a perfusion catheter.

It would be advantageous therefore to provide a re-routing means such as a guidewire so that the new catheter could be securely and safely inserted back to the original stenotic area of the patient's vasculature. Such a mechanism is provided by the fixed wire angioplasty catheter of the present device.

Currently available fixed wire catheters have no inherent bailout provision. These devices require complete removal and re-routing of the catheter if an exchange becomes necessary. Such a re-route is usually under emergency conditions. These maneuvers may cause danger and risk to the patient since reinsertion of a balloon or perfusion catheter may not be possible during such an emergency due to obliteration or occlusion of the vessel channel. Either procedure increases the risk to a patient by taking extra time in an emergency.

Referring now to FIG. 9, before removing the original catheter 10, one method of using the present device comprises inserting a guidewire 33 into the bailout lumen 20 until it protrudes from a guidewire distal opening 34 and is aligned in parallel with the tip of the torquewire 32. With the guidewire now in place inside the bailout lumen 20, the catheter 10 can be retracted from the vasculature and patient while the guidewire 33 remains in its position in the patient. A new catheter can then be slid distally over the guidewire 33, advancing to the same place as the original catheter 10.

Another aspect of the present invention catheter is a low profile catheter which inherently may readily and rapidly be converted from one mode of use to the other. Thus, the catheter can be used first as a rapid exchange catheter, with the guidewire extending in the bailout lumen 20 only from the side port 44 to the distal end of the catheter 34. It can then be converted from this rapid exchange mode of use to conventional over-the-wire use simply by removing the guidewire and, while maintaining the catheter 10 in place in the patient, inserting a new guidewire 33 into the proximal end 21 of the bailout lumen 20 and extending the guidewire 33 out of the distal end 34 of the catheter.

With a guidewire 33 extending the entire length of the bailout lumen 20, the catheter can be removed and reinserted as a rapid exchange catheter. With the guidewire 33 extending proximally out of the proximal opening 21, the guidewire 33 is maintained in position in the patient while the guidewire is moved laterally out of the outside wall 36 of the bailout lumen 20 through the guidewire removing means 46 in the direction indicated by arrow 51 (FIGS. 9 and 10). The catheter 10 is pulled back proximally until the distal end 14 of the catheter 10 is outside of the patient. During this portion of the procedure, the guidewire 33 is held stationary by grasping it at the proximal end. Then the operator may hold the guidewire 33 by grasping the portion of the guidewire 33 exposed at the distal end 14 of the catheter 10, remove the catheter 10 off of the proximal end of the guidewire 33, and insert a new catheter of any type over the guidewire 33 while maintaining the position of the tip of guidewire 33 in the patient's vascular system. The insertion of the new catheter 10 may be accomplished in rapid exchange mode by retrograde insertion of the proximal end of the guidewire 33 through the distal end 34 of the bailout lumen 20 and out of the side port 44. The proximal end of the guidewire is then held in position while the catheter 10 is advanced forward into the patient.

Alternatively, if desired, the guidewire 33 may be removed with the catheter maintained in position, and in a matter of seconds the guidewire may be reinserted through the proximal opening 21 of the catheter shaft 11 to convert back to bailout function.

Thus, it will be appreciated that the low profile fixed wire catheter of the present invention can easily be used in either a rapid exchange mode or an over the wire mode; that conversion between modes of use may be readily accomplished; that guidewire exchange may be accomplished in either mode of use, and that catheter exchange when in either mode of use can be accomplished without use of an extension guidewire; and that all of the forgoing conversions and modes of use can be accomplished while maintaining the positioning of either the guidewire or the catheter in the patient.

Thus, one method of the present invention comprises inserting the guidewire 33 through the bailout lumen 20 of the catheter illustrated in FIG. 9, (which is already in place in a patient) with the guidewire 33 passing through the proximal opening 21 (FIG. 3) of the bailout lumen 20 and extending from that point distally through the bailout lumen and out of the distal end 34 thereof. The guidewire 33 can then be exchanged by removing it and reinserting it through the proximal opening 21.

The catheter can be exchanged by holding the guidewire stationary as explained above while the catheter is being withdrawn so that the guidewire 33 is pulled through the guidewire removing means 46 until the distal end of the catheter is outside the patient. Specifically, as shown in FIGS. 9 and 10, a guidewire 33 is first inserted into the empty bailout lumen 20 and advanced distally until reaching and traversing the distal end 34 of the bailout lumen 20. Referring to FIG. 9, while the catheter 10 is being removed from the patient, the guidewire 33 is pulled laterally, in the direction indicated by the arrow 51, through the guidewire removing means 46. As the catheter 10 emerges from the guiding catheter and patient, the guidewire 33 transits laterally through the guidewire removing means 46 thereby negating the need for an exterior guidewire extension. Referring to FIG. 10, the guidewire 33 can thereafter be laterally removed from the guidewire removing means 46 in the bailout lumen 20 even further until reaching the side port 44.

The guidewire 33 is then held distally of the catheter and a new catheter is inserted, this time in rapid exchange mode. Once the new catheter is in place, the guidewire can be removed or can be exchanged (if desired) to convert the catheter back into the over-the-wire mode of use as explained above.

Angioplasty Methods For Fixed Wire Angioplasty

Referring to FIG. 11, a set of four panels FIGS. 11a, 11b, 11c, and 11d sequentially illustrate one clinical scenario using the fixed-wire/bail-out angioplasty catheter 10. In FIG. 11a, the deflated balloon 24 of the catheter 10 is inserted into a stenotic area 50 of a patient's vasculature 49. The catheter 10 is steered to the patient's stenotic region by manipulating the torquewire tip 32. Once the balloon 24 is positioned in the vessel at the stenotic lesion 50, it is inflated by a fluid media as illustrated in FIG. 11b.

The balloon 24 is then deflated and advanced distally past the stenotic lesion 50 (FIG. 11c) so that the distal guidewire lumen 34 is past the lesion previously dilated. At this point a guidewire 33 is inserted into the bailout lumen 20 and advanced distally until it emerges from the distal guidewire opening 34. The guidewire 33 is then advanced further distally until it extends in parallel to the catheter tip 32 of the torquewire 26. Once the guidewire 33 is aligned or distal to the torquewire tip 32, the fixed-wire catheter 10 can be removed from the patient leaving the guidewire 33 in place (FIG. 11*d*). Once the balloon catheter has been completely removed from the patient, the physician has the option of reinserting another catheter over the guidewire 33 into the stenosis as part of a bailout procedure.

FIG. 12 describes a second clinical scenario illustrated by FIGS. 12*a*–12*d*. In FIG. 12 the catheter 10, having an angioplasty balloon 24, is first positioned at a point immediately proximal to the stenotic lesion 50 (FIG. 12*a*). The guidewire 33 is then advanced through the bailout lumen 20 distally until it emerges from the distal opening 34. The guidewire 33, with its tip out of the catheter 20 but inside the vessel 49 is then advanced further passing through and beyond the stenotic lesion 50. The catheter 10 is then steered over the in-place guidewire 33 distally so that the balloon 24 is positioned inside the lesion 50 (FIG. 12*b*). A fluid can then be injected into the balloon inflation lumen 16 inflating the balloon 24 and dilating lesion 50. The balloon can preferably be inflated and deflated repeatedly, allowing blood flow between cycles, until the lesion is fully dilated. After dilation, the balloon 24 is deflated (FIG. 12*c*) by withdrawing the fluid from the balloon inflation lumen 16, and the catheter 10 removed leaving the guidewire 33 in place so that another angioplasty catheter can be safely employed over the wire if necessary (FIG. 12*d*).

Another alternate clinical scenario is illustrated in FIGS. 13*a*–13*d*. In this scenario, the catheter 10 is inserted into a patient and moved distally into the stenosis 50. The stenotic lesion 50 is then dilated by inflation of the balloon 24 (FIG. 13*a*). After dilation, the balloon 24 is deflated and the guidewire 33 is inserted into the bailout lumen proximal opening 21 and advanced distally until it exits the distal opening 34 (FIG. 13*b*). The guidewire 33 is then advanced further, through and beyond the just dilated lesion 50, while the deflated balloon 24 remains in place (FIG. 13*c*). After the guidewire 33 is positioned distal to the lesion 50 the balloon catheter 10 can be withdrawn leaving the guidewire 33 in place so that further angioplasty catheters can be easily inserted, if necessary (FIG. 13*d*).

In some instances a patient's vasculature has more than one stenotic lesion. FIGS. 14*a* through 14*h* illustrate a double lesion of bifurcation at points 50, 54. In this case the patient has a vascular "Y" junction 56 at a point proximal to the lesions 50, 54. This patient therefore requires a double angioplasty procedure with balloon dilation at each stenotic lesion. The clinical scenario is outlined in FIGS. 14*a*–14*h*. In order to treat both lesions 50, 54 the fixed-wire catheter 10 is first placed at lesion 50 and the guidewire 33 is positioned passing through the second lesion 54 (FIG. 14*a*). The first lesion 50 is then dilated by inflation of the balloon 24 (FIG. 14*b*). After dilation, the position of the guidewire 33 and balloon catheter 10 are switched bringing the balloon 24 in contact with the second lesion 54 and the guidewire 33 passing through the first lesion 50 (FIGS. 14*c* and 14*d*). The balloon 24 is again inflated with fluid causing dilation of the second stenotic lesion 54 (FIG. 14*e*). After completing dilation of the second lesion 54, the balloon catheter 10 can be removed leaving the guidewire 33 in place so that further angioplasty procedures can be carried out if necessary (FIG. 14*f*).

Bailout of Other Intravascular Catheters

As mentioned above, the present invention is also applicable to bailing out other intravascular catheters, including angioplasty catheters. Intravascular catheters contemplated in accordance with the present invention include any intravascular catheter having a means attached, mounted, or included on the distal portion of the catheter for use in a diagnostic or therapeutic procedure. Such means can include, by way of example, angioplasty balloons and/or means such as those used in laser procedures, atherectomy procedures, stent deployment, intravascular imaging systems, or otherwise.

The catheter can be a fixed wire catheter as described above. Or, the catheter may be of another arrangement. For example, FIG. 15 illustrates a cross-sectional view of an over-the-wire angioplasty catheter incorporating the bailout lumen in accordance with the present invention.

In FIG. 15, an intravascular catheter 60 having a catheter shaft 61 with a proximal opening 63 in a proximal portion 62 and a distal opening 64 in a distal portion 65 is provided. In the pictured embodiment, the proximal opening 63 and the distal opening 64 are in, respectively, the proximal end 66 and the distal end 67. An angioplasty balloon 68 (or some other diagnostic or therapeutic means) is mounted on the distal portion 65. The angioplasty balloon 68 is inflated and deflated through the balloon inflation lumen 69 that extends from the proximal portion 62 of the catheter shaft 61, through the shaft 61, and terminates in the balloon 68.

Also in the illustrated embodiment, a guidewire lumen 70 extends from the proximal opening 63 to the distal opening 64. The guidewire lumen 70 is adapted to receive a steerable guidewire 71 along its entire length. The catheter shaft 61 additionally comprises an outside wall 72.

A bailout lumen 73 is attached to the outside wall 72 of the catheter shaft and runs distally from the proximal portion 62 toward the distal portion 65 of the catheter shaft 61, preferably terminating at a point somewhat proximally of the balloon 68. The bailout lumen 73 has a proximal opening 74 in a proximal end 78 and a distal opening 75 in a distal end 79 and is adapted to receive a guidewire extending along its entire length through the interior of the bailout lumen 80. The bailout lumen has an outside wall 76.

In a preferred embodiment, the bailout lumen 73 additionally comprises a side port 77, as is shown and discussed in greater detail in connection FIG. 2 for a fixed wire catheter. Further, in highly preferred embodiments, the bailout lumen 73 can also comprise guidewire removing means, which is shown and discussed in greater detail in connection with the discussion of FIGS. 3–5 for a fixed wire catheter.

The methods of use of the vascular catheters in accordance with the present invention are substantially similar to the uses described above in connection with the procedures for bailout of a fixed wire catheter.

For example, in the case of rapid-exchange type catheters, the procedures for guidewire exchange can be accomplished in accordance with the present invention and the above discussion. As will be appreciated, the catheter exchange procedures of other vascular catheters are virtually identical for those discussed above for fixed wire catheters.

The present invention has been described in certain preferred embodiments. Such embodiments are ilustrative rather than limiting. The scope of the invention should therefore be construed in accordance with the appended claims and any equivalents thereof.

What is claimed is:

1. An intravascular catheter, comprising:

a catheter shaft having a proximal end, a distal portion, an outer wall, a distal end, and an interior lumen extending therethrough, and having diagnostic or therapeutic means mounted on the distal portion;

a bailout lumen attached to the outer wall of said catheter shaft, said bailout lumen having a proximal opening and a distal opening, said lumen extending along the outer wall of said catheter shaft from a point within about 30 cm of the proximal end of the catheter to a point proximal to and within about 30 cm of said diagnostic or therapeutic means, said bailout lumen adapted to receive a removable guidewire and having an outer wall.

2. The catheter of claim 1, wherein said catheter further comprises guidewire removing means disposed in said outer wall of said bailout lumen, adapted for removing a guidewire laterally through the outer wall of said bailout lumen.

3. The catheter of claim 1, wherein said outer wall of said bailout lumen further comprising a side port extending therethrough, located near said distal opening, said side port adapted to permit a guidewire to extend therethrough to pass through a distal portion of the bailout lumen.

4. The catheter of claim 1, wherein said bailout lumen further comprises a rigid proximal portion and a collapsible distal portion.

5. An intravascular catheter, comprising:
   a catheter shaft having a proximal end, a distal portion, an outer wall, a distal end, and an interior lumen extending therethrough, and having diagnostic or therapeutic means mounted on the distal portion;
   a bailout lumen attached to the outer wall of said catheter shaft, said bailout lumen having a proximal opening and a distal opening, said lumen extending along the outer wall of said catheter shaft from a point within about 30 cm of the proximal end of the catheter to a point proximal to and within about 30 cm of said diagnostic or therapeutic means, said bailout lumen adapted to receive a removable guidewire and having an outer wall, said outer wall further comprising guidewire removing means extending from the proximal opening of the bailout lumen distally toward the diagnostic or therapeutic means at least 30 cm., said guidewire removing means being adapted to permit a guidewire extending through the bailout lumen to be removed laterally through the outer wall.

6. The catheter of claim 5, wherein said outer wall of said bailout lumen has a side port extending therethrough, said side port located near the distal end of said bailout lumen and adapted to permit a guidewire to extend therethrough to pass through a distal portion of said bailout lumen.

7. An angioplasty catheter, comprising:
   a catheter shaft having a proximal end, a distal portion, an outer wall, a distal end, and an interior lumen extending therethrough, and a balloon inflation lumen extending therethrough;
   an angioplasty balloon mounted on the distal portion of said catheter operatively communicating with said balloon inflation lumen for inflation and deflation of said balloon; and
   a bailout lumen attached to the outer wall of said catheter shaft, said bailout lumen having a proximal opening and a distal opening, said lumen extending along said catheter shaft from a point within about 30 cm of the proximal end of the catheter to a point proximal to and within about 30 cm of said balloon, said bailout lumen adapted to receive a removable guidewire and having an outer wall, said outer wall further comprising a side port extending therethrough, located near said distal opening, said side port adapted to permit a guidewire to extend therethrough to pass through a distal portion of the bailout lumen.

8. The catheter of claim 7, wherein said catheter further comprises guidewire removing means, adapted for removing a guidewire laterally out of said bailout lumen.

9. The catheter of claim 7, wherein said bailout lumen further comprises a rigid proximal portion and a collapsible distal portion.

10. A method of performing bailout of an intravascular catheter comprising:
    advancing a catheter as defined in claim 1 into a patient's vasculature;
    advancing a guidewire through the proximal end of the bailout lumen and out the distal end of said bailout lumen and into a desired location in the patient's vasculature;
    removing the catheter while maintaining the guidewire in the desired location in the patient's vasculature; and
    inserting the proximal end of the guidewire into the bailout lumen or the interior lumen of a second catheter as defined in claim 1; and
    advancing the second catheter over the guidewire and into the desired position in the patient's vasculature.

11. A method of performing bailout of an intravascular guidewire having a distal and a proximal end, comprising:
    advancing the distal end of the guidewire into a patient's vasculature through the proximal end of the bailout lumen of a catheter as defined in claim 1 and out the distal end of said lumen and into a desired location in the patient's vasculature;
    advancing the catheter over the guidewire and into a desired location in the patient's vasculature;
    removing the guidewire laterally through the outer wall of the bailout lumen while maintaining the catheter in the desired location in the patient's vasculature; and
    inserting the distal end of a second guidewire into the patient's vasculature and advancing said second guidewire through the bailout lumen or the interior lumen of the catheter.

12. A method of performing rapid exchange of an intravascular catheter comprising:
    advancing a guidewire through the side port in the outer wall of a catheter as defined in claim 9 and out the distal end of the catheter;
    positioning the distal end of the guidewire in a desired location in the patient's vasculature;
    advancing the catheter over the guidewire and into a desired location in the patient's vasculature;
    removing the catheter while maintaining the guidewire in the desired location in the patient's vasculature; and
    inserting the proximal end of the guidewire into the distal end of the bailout lumen or the interior lumen of a second catheter as defined in claim 9, and advancing the guidewire until it emerges out the proximal end of the second catheter; and
    advancing the second catheter over the guidewire and into the desired position in the patient's vasculature.

13. The method of claim 12, wherein said proximal end of the guidewire is inserted into the distal end of the second catheter and advanced through side port in the outer wall of the bailout lumen.

14. An angioplasty catheter, comprising:
    a catheter shaft having a proximal end, a distal portion, an outer wall, a distal end, and an interior lumen extending therethrough, and a balloon inflation lumen extending therethrough;
    an angioplasty balloon on the distal portion of said catheter operatively communicating with said balloon inflation lumen for inflation and deflation of said balloon; and a bailout lumen attached to said outer wall of said catheter shaft, said bailout lumen having a proximal opening and a distal opening, said lumen extending along said catheter shaft from a point within about 30 cm of the proximal end of the catheter to a point proximal to and within about 30 cm of said balloon, said bailout lumen adapted to receive a removable guidewire and having an outer wall, said outer wall further comprising guidewire removing means extending from the proximal opening of the bailout lumen distally toward the balloon at least 30 cm., said guidewire removing means being adapted to permit a guidewire extending through the bailout lumen to be removed laterally through the outer wall.

15. The catheter of claim 14, wherein said outer wall of said bailout lumen has a side port extending therethrough, said side port located near the distal end of said bailout lumen and adapted to permit a guidewire to extend therethrough to pass through a distal portion of said bailout lumen.

* * * * *